(12) United States Patent
Gleason, Sr.

(10) Patent No.: US 11,760,862 B2
(45) Date of Patent: *Sep. 19, 2023

(54) COMPOSITE PANEL

(71) Applicant: Composite Technologies International, LLC, Anniston, AL (US)

(72) Inventor: Stephen Gleason, Sr., Burr Ridge, IL (US)

(73) Assignee: Composite Technologies International, LLC, Anniston, AL (US)

(*) Notice: Subject to any disclaimer, the term of this patent is extended or adjusted under 35 U.S.C. 154(b) by 1 day.

This patent is subject to a terminal disclaimer.

(21) Appl. No.: 17/322,372

(22) Filed: May 17, 2021

(65) Prior Publication Data

US 2021/0277204 A1  Sep. 9, 2021

Related U.S. Application Data

(63) Continuation of application No. 15/830,808, filed on Dec. 4, 2017, now Pat. No. 11,008,438.

(Continued)

(51) Int. Cl.
*C08K 3/30* (2006.01)
*G01N 1/36* (2006.01)
(Continued)

(52) U.S. Cl.
CPC .............. *C08K 3/30* (2013.01); *C08J 5/043* (2013.01); *C08J 5/18* (2013.01); *C08J 5/244* (2021.05); *C08J 5/249* (2021.05); *G01N 1/36* (2013.01); *G01N 33/442* (2013.01); *B29C 37/0025* (2013.01); *B29C 41/00* (2013.01);

(Continued)

(58) Field of Classification Search
None
See application file for complete search history.

(56) References Cited

U.S. PATENT DOCUMENTS

| 3,764,247 A | 10/1973 | Garrett |
| 3,889,035 A | 6/1975 | Jakes |

(Continued)

FOREIGN PATENT DOCUMENTS

| CA | 1082051 A | 7/1980 |
| CN | 101792569 A | 8/2010 |
| JP | 01038222 A | 2/1989 |

OTHER PUBLICATIONS

Office Action Document from Canadian Application No. 2,987,622; dated Jan. 7, 2019.

*Primary Examiner* — Vivian Chen
(74) *Attorney, Agent, or Firm* — Neustel Law Offices

(57) ABSTRACT

A composite core material and methods for making same are disclosed herein. The composite core material comprises mineral filler discontinuous portions disposed in a continuous encapsulating resin. Further, the method for forming a composite core material comprises the steps of forming a mixture comprising mineral filler, an encapsulating prepolymer, and a polymerization catalyst; disposing the mixture onto a moving belt; and polymerizing said encapsulating prepolymer to form a composite core material comprising mineral filler discontinuous portions disposed in a continuous encapsulating resin.

15 Claims, 2 Drawing Sheets

Related U.S. Application Data

(60) Provisional application No. 62/429,535, filed on Dec. 2, 2016.

(51) Int. Cl.

| | |
|---|---|
| *C08J 5/24* | (2006.01) |
| *C08J 5/04* | (2006.01) |
| *C08J 5/18* | (2006.01) |
| *G01N 33/44* | (2006.01) |
| *C08K 3/013* | (2018.01) |
| *C08L 35/02* | (2006.01) |
| *B29C 70/70* | (2006.01) |
| *B29C 41/30* | (2006.01) |
| *B29C 70/30* | (2006.01) |
| *B29C 70/68* | (2006.01) |
| *B29C 70/86* | (2006.01) |
| *B29C 70/02* | (2006.01) |
| *B29C 37/00* | (2006.01) |
| *B29C 41/20* | (2006.01) |
| *B29C 70/54* | (2006.01) |
| *B29C 70/60* | (2006.01) |
| *B29C 41/00* | (2006.01) |
| *B29C 70/88* | (2006.01) |
| *B29C 41/32* | (2006.01) |
| *B29C 41/22* | (2006.01) |
| *B29K 31/00* | (2006.01) |
| *B29K 67/00* | (2006.01) |
| *B29K 105/06* | (2006.01) |
| *B29K 105/16* | (2006.01) |
| *B29K 267/00* | (2006.01) |
| *B29K 231/00* | (2006.01) |
| *B29K 105/20* | (2006.01) |
| *B29K 309/00* | (2006.01) |
| *B29K 303/04* | (2006.01) |
| *B29K 631/00* | (2006.01) |
| *B29K 667/00* | (2006.01) |
| *B29K 509/00* | (2006.01) |
| *B29K 303/00* | (2006.01) |
| *G01N 3/10* | (2006.01) |

(52) U.S. Cl.
CPC ............ *B29C 41/003* (2013.01); *B29C 41/20* (2013.01); *B29C 41/22* (2013.01); *B29C 41/30* (2013.01); *B29C 41/32* (2013.01); *B29C 70/02* (2013.01); *B29C 70/30* (2013.01); *B29C 70/305* (2013.01); *B29C 70/545* (2013.01); *B29C 70/60* (2013.01); *B29C 70/68* (2013.01); *B29C 70/682* (2013.01); *B29C 70/70* (2013.01); *B29C 70/86* (2013.01); *B29C 70/865* (2013.01); *B29C 70/88* (2013.01); *B29K 2031/00* (2013.01); *B29K 2067/00* (2013.01); *B29K 2067/06* (2013.01); *B29K 2105/06* (2013.01); *B29K 2105/16* (2013.01); *B29K 2105/20* (2013.01); *B29K 2231/00* (2013.01); *B29K 2267/00* (2013.01); *B29K 2267/06* (2013.01); *B29K 2303/00* (2013.01); *B29K 2303/04* (2013.01); *B29K 2309/00* (2013.01); *B29K 2509/00* (2013.01); *B29K 2631/00* (2013.01); *B29K 2667/00* (2013.01); *B29K 2667/06* (2013.01); *C08J 2300/12* (2013.01); *C08J 2335/02* (2013.01); *C08J 2367/00* (2013.01); *C08K 3/013* (2018.01); *C08K 2003/3045* (2013.01); *C08L 35/02* (2013.01); *G01N 3/10* (2013.01); *G01N 2001/364* (2013.01)

(56) References Cited

U.S. PATENT DOCUMENTS

| | | |
|---|---|---|
| 4,016,112 A | 4/1977 | Kajiura |
| 4,028,158 A | 6/1977 | Hipchen |
| 4,061,613 A | 12/1977 | Self |
| 4,061,614 A | 12/1977 | Self |
| 4,099,280 A | 7/1978 | Hoppe |
| 4,136,215 A | 1/1979 | den Otter |
| 4,192,791 A | 3/1980 | Self |
| 4,200,697 A | 4/1980 | Blount |
| 4,216,294 A | 8/1980 | Halle |
| 4,284,683 A | 8/1981 | Hipchen |
| 4,386,166 A | 5/1983 | Peterson |
| 4,388,419 A | 6/1983 | Murakami |
| 4,438,166 A | 3/1984 | Gluck |
| 4,461,850 A | 7/1984 | Carignani |
| 4,572,865 A | 2/1986 | Gluck |
| 4,595,623 A | 6/1986 | Du Pont |
| 4,753,837 A | 6/1988 | Hanusa |
| 4,801,483 A | 1/1989 | Beckerman |
| 4,916,004 A | 4/1990 | Ensminger |
| 5,089,544 A | 2/1992 | Ross |
| 5,091,436 A | 2/1992 | Frisch |
| 5,221,386 A | 6/1993 | Ensminger |
| 5,242,637 A | 9/1993 | Inoue |
| 5,254,598 A | 10/1993 | Schlameus |
| 5,281,674 A | 1/1994 | Klaiber |
| 5,305,568 A | 4/1994 | Beckerman |
| 5,447,921 A | 9/1995 | Borden |
| 5,498,645 A | 3/1996 | Mariano |
| 5,665,785 A | 9/1997 | McClellan |
| 5,685,934 A | 11/1997 | Ikeda |
| 5,900,311 A | 5/1999 | Campanella |
| 6,060,124 A | 5/2000 | Ikegawa |
| 6,103,032 A | 8/2000 | Greve |
| 6,119,750 A | 9/2000 | Greve |
| 6,231,970 B1 | 5/2001 | Andersen |
| 6,340,194 B1 | 1/2002 | Muirhead |
| 6,476,111 B1 | 11/2002 | Beauchemin |
| 6,545,066 B1 | 4/2003 | Immordino, Jr. |
| 7,150,915 B2 | 12/2006 | Kia |
| 7,205,066 B1 | 4/2007 | Hammi |
| 8,915,996 B2 | 12/2014 | Novak |
| D744,014 S | 11/2015 | Gleason |
| 9,217,072 B2 | 12/2015 | Novak |
| 10,612,237 B1* | 4/2020 | Gleason .................. E04C 2/22 |
| 11,008,438 B2* | 5/2021 | Gleason, Sr. ............ C08K 3/30 |
| 11,377,849 B2* | 7/2022 | Gleason .................. B29C 70/66 |
| 2002/0016420 A1 | 2/2002 | Zarnoch |
| 2003/0165670 A1 | 9/2003 | Gerard |
| 2005/0281999 A1 | 12/2005 | Hofmann |
| 2007/0107189 A1 | 5/2007 | Prichard |
| 2007/0243995 A1 | 10/2007 | Dallies |
| 2008/0127604 A1 | 6/2008 | Schiffmann |
| 2008/0287575 A1 | 11/2008 | Terry Lee |
| 2010/0189973 A1 | 7/2010 | Mikkelsen |
| 2010/0209651 A1 | 8/2010 | Mikkelsen |
| 2010/0239847 A1 | 9/2010 | Darby |
| 2010/0276542 A1 | 11/2010 | Rouyre |
| 2013/0273341 A1 | 10/2013 | Albertelli |
| 2018/0022045 A1 | 1/2018 | Sebastian |
| 2018/0155521 A1* | 6/2018 | Gleason, Sr. ............ C08K 3/30 |
| 2019/0184365 A1 | 6/2019 | Gleason |
| 2020/0232218 A1 | 7/2020 | Gleason |
| 2022/0001349 A1* | 1/2022 | Gleason .................. C08L 27/06 |

\* cited by examiner

COMPOSITE PANEL

CROSS REFERENCE TO RELATED APPLICATIONS

The present application is a continuation of U.S. application Ser. No. 15/830,808 filed on Dec. 4, 2017 which issues as U.S. Pat. No. 11,008,438 on May 18, 2021, which claims priority to U.S. Provisional Application No. 62/429,535 filed Dec. 2, 2016. Each of the aforementioned patent applications is herein incorporated by reference in their entirety.

STATEMENT REGARDING FEDERALLY SPONSORED RESEARCH OR DEVELOPMENT

Not applicable to this application.

BACKGROUND

The described example embodiments in general relate to a composite core material, methods of making same, methods of making a composite material with same, and of testing compressive strength thereof.

A composite material (also called a composition material or shortened to composite) is a material made from two or more constituent materials with significantly different physical or chemical properties that, when combined, produce a material with characteristics different from the individual components. The individual components remain separate and distinct within the finished structure. The new material may be preferred for many reasons: common examples include materials which are stronger, lighter, or less expensive when compared to traditional materials.

Transportation, construction and aerospace are the largest market segments within the composites industry recently, representing 62 percent of its total value. Development of low-cost and high-strength composite material to be used in those industries is important.

DETAILED DESCRIPTION

Figure 1:
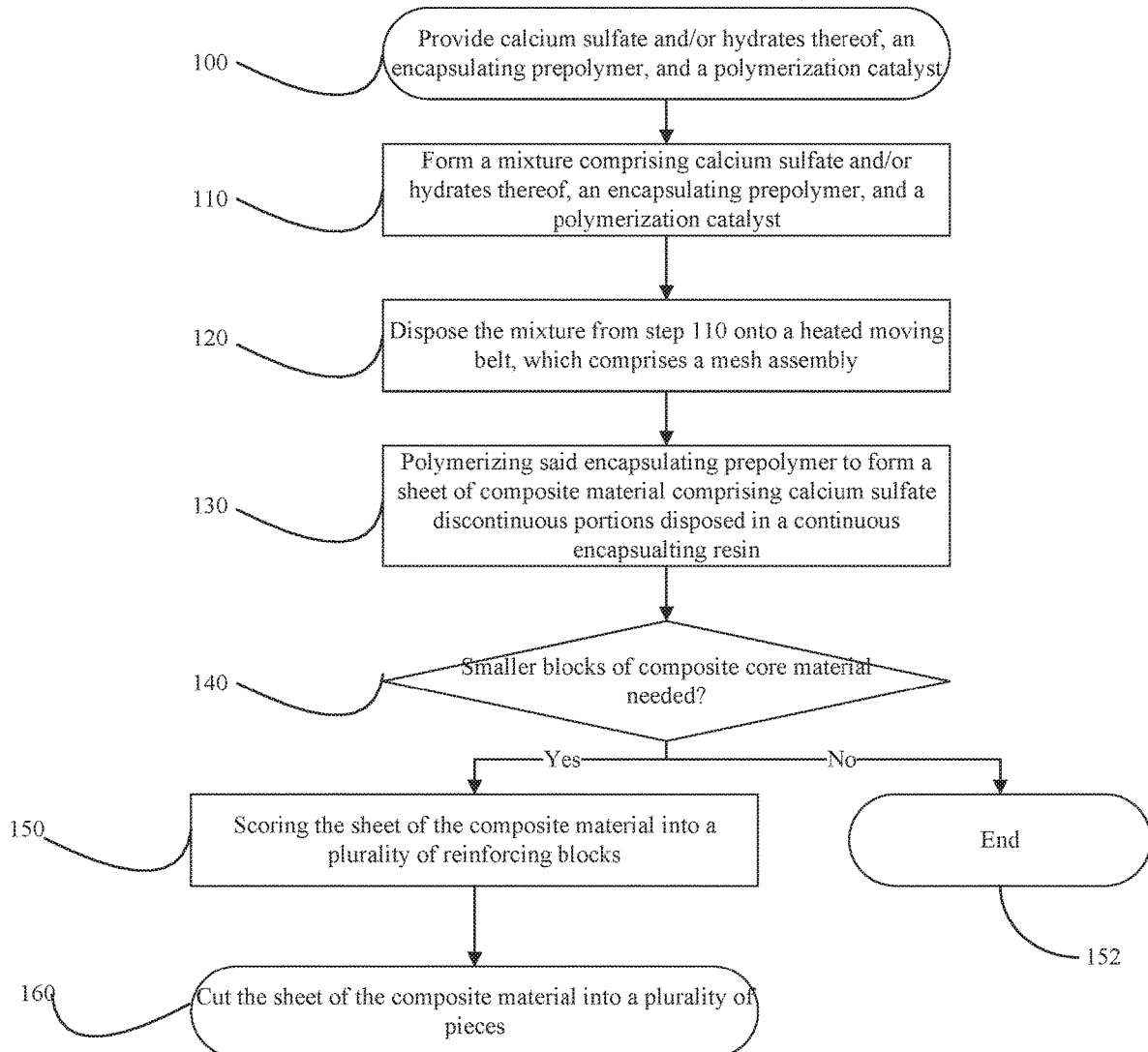
FIG. 1 illustrates a flow chart of forming a composite core material.

Some of the various embodiments of the present disclosures are described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of embodiments disclosed herein may be combined in any suitable manner in one or more embodiments. In the following description, numerous specific details are recited to provide a thorough understanding of embodiments of the invention. One skilled in the relevant art will recognize, however, that the embodiments may be practiced without one or more of the specific details, or with other methods, components, materials, and so forth. In other instances, well-known structures, materials, or operations are not shown or described in detail to avoid obscuring aspects of the claimed invention.

Embodiments of Applicant's disclosure describe compositions of a composite core material, methods to form same, methods to form a composite material with same, and methods to test the compressive strength of same.

In certain embodiments, a composite core material comprises one or more mineral filler discontinuous portions disposed in a continuous encapsulating resin. In certain embodiments, the mineral filler is calcium sulfate. In other embodiments, the mineral filler is calcium carbonate. In other embodiments, the mineral filler is aluminum trihydrate. In other embodiments, the mineral filler is talc. In other embodiments, the mineral filler is gypsum. In other embodiments, the mineral filler is magnesium hydroxide. In other embodiments, the mineral filler is dolomite. In other embodiments, the mineral filler is any combination of calcium sulfate, calcium carbonate, aluminum trihydrate, talc, gypsum, magnesium hydroxide, and dolomite.

Further, in certain embodiments, the calcium sulfate comprises hydrates thereof. In certain embodiments a calcium sulfate hydrate is calcium sulfate hemihydrate having a formula of $CaSO_4 \cdot (nH_2O)$, wherein n is equal to or greater than 0.5 and equal to or less than 0.8. In other embodiments, the calcium sulfate hydrate is calcium sulfate di hydrate having a formula of $CaSO_4 \cdot 2H_2O$. In yet other embodiments, the calcium sulfate hydrate can be a combination of calcium sulfate hemihydrate and calcium sulfate dihydrate. The weight percentage of the calcium sulfate hemihydrate in the combination of calcium sulfate hemihydrate and calcium sulfate dihydrate ranges from about 5% to about 95%, e.g., 10%, 15%, 20%, 25%, 30%, 35%, 40%, 45%, 50%, 55%, 60%, 65%, 70%, 75%, 80%, 85%, 90% or another concentration of the calcium sulfate dihydrate can be from about 5% to about 95%. The weight percentage of the calcium sulfate dihydrate ranges from about 95% to about 5%, e.g., 90%, 85%, 80%, 75%, 70%, 65%, 60%, 55%, 50%, 45%, 40%, 35%, 30%, 25%, 20%, 15%, 10% or another concentration of the calcium sulfate dihydrate can be from about 95% to about 5%. As used herein, "about" is used to describe a difference of 10% in any measurements.

In some embodiments, the continuous encapsulating resin is a polymerized product of polyester resins having a structure of:

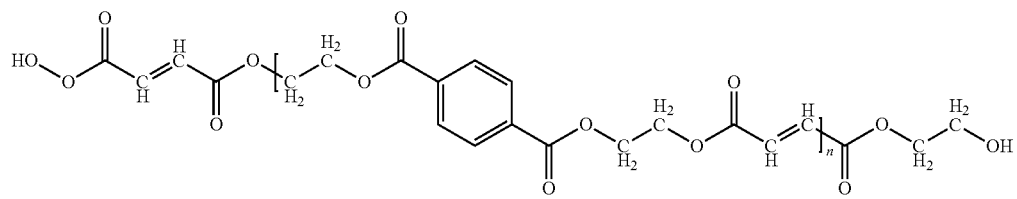

wherein n is from about 3 to about 6. In some embodiments, the polyester resins are 404 Isophthalic Resin purchased from US Composites. The polylite polyester resin 404 is a rigid, medium reactivity, premium chemical resistant, isophthalic based. This resin has low viscosity and is thixotropic. In other embodiments, the polyester resins are AROPOL unsaturated polyester resins purchased from Ashland. In yet other embodiments, the polyester resins are HETRON FR 650 Series flame retardant resins purchased from Ashland. Composites made with HETRON FR 650 Series resins have been tested and have achieved a Class 1 Flame Spread per ASTM E-84 without addition of synergists such as antimony trioxide. In still yet other embodiments, MODAR acrylic modified resins purchased from Ashland are used to achieve fire retardant effects in the composite core materials. These two examples of the fire retardant resins are not meant to be limiting as other fire retardant resins may be used.

In other embodiments, the continuous encapsulating resin is a polymerized product of vinyl ester resins having a structure of:

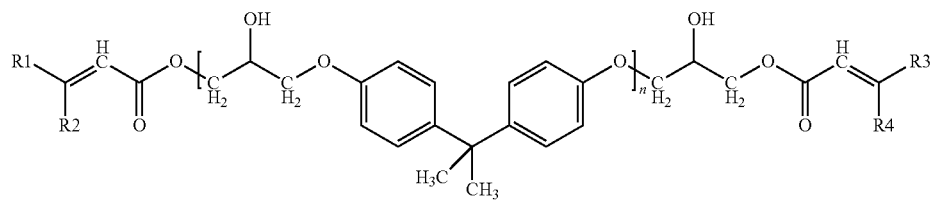

wherein n is 1 to about 2, where $R_1$ is hydrogen or alkyl, $R_2$ is hydrogen or alkyl, $R_3$ is hydrogen or alkyl, $R_4$ is hydrogen or alkyl. In some embodiments, the vinyl ester resins are TAP Marine vinyl ester resin purchased from TAP Plastics.

In yet other embodiments, the continuous encapsulating resin is a polymerized product of a combination of the polyester resins and the vinyl ester resins. The weight percentage of the polyester resin ranges from about 5% to about 95%, e.g., 10%, 15%, 20%, 25%, 30%, 35%, 40%, 45%, 50%, 55%, 60%, 65%, 70%, 75%, 80%, 85%, 90% or another concentration of the polyester resin from can be from about 5% to about 95%. The weight percentage of the vinyl ester resin ranges from about 95% to about 5%, e.g., 90%, 85%, 80%, 75%, 70%, 65%, 60%, 55%, 50%, 45%, 40%, 35%, 30%, 25%, 20%, 15%, 10% or another concentration of the vinyl ester resin from can be from about 95% to about 5%.

In yet another embodiment, the continuous encapsulating resin comprises about 38.3139% by weight styrene, about 0.3% by weight dimethylaniline, about 0.195% by weight cobalt-2-ethylhexanoate.

The respective weight percentages of the calcium sulfate discontinuous portion and the continuous encapsulating resins in the composite core material can vary. In some embodiments, the composite core material comprises about 60% to about 80% by weight the calcium sulfate discontinuous portion and about 20% to about 40% by weight the continuous encapsulating resins. In other embodiments, the composite core material comprises about 80% by weight the calcium sulfate discontinuous portion and about 20% by weight the continuous encapsulating resins and the composite core material has a density of about 2 lbs/feet$^2$.

FIG. 1 summarizes an embodiment of a method to make the composite core material. Referring to FIG. 1, in step 100, calcium sulfate and/or hydrates thereof, an encapsulating prepolymer, and a polymerization catalyst are provided. In some embodiments, calcium sulfate dihydrate having a formula of $CaSO_4.2H_2O$. In other embodiments, calcium sulfate hemihydrate having a formula of $CaSO_4.(nH_2O)$, wherein n is equal to or greater than 0.5 and equal to or less than 0.8. In some embodiments, polyester resins are used. In other embodiments, vinyl ester resins are used. In yet other embodiments, styrene-based resins are used. In some embodiments, a polymerization catalyst is 2-Butanone peroxide, having a structure of

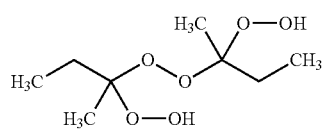

2-Butanone peroxide has a molecular weight of about 210.22 and a density of about 1.053 g/ml at 20.degree. C. In other embodiments, any catalyst known to a person in the art that can facilitate the polymerization of the encapsulating resin to encapsulate the discontinuous calcium sulfate portions can be employed.

In step 110, all the materials provided in step 100 are mixed to form a first mixture comprising calcium sulfate and/or hydrates thereof, the encapsulating prepolymer, and the polymerization catalyst. In certain embodiments, the polymerization catalyst has a concentration of about 1% to 2.5% by weight in a second mixture of the encapsulating prepolymer and the polymerization catalyst. The weight percentage of the polymerization catalyst can be about 1%, 1.25%, 1.5%, 1.75%, 2%, 2.25%, or any other weight percentage that ranges from 1% to 2.5%.

Now in step 120, the first mixture comprising calcium sulfate and/or hydrates thereof, an encapsulating prepolymer, and a polymerization catalyst is poured onto a moving belt. In certain embodiments, the moving belt is heated to facilitate the polymerization of the encapsulating prepolymer. In certain embodiments, a mesh assembly lays on top of the moving belt and the first mixture is spread evenly over the mesh assembly. In some embodiments, the mesh assembly has a width of about 20 inches to about 60 inches. In other embodiments, the mesh assembly has a width of 24 inches. In some embodiments, the mesh assembly is a fiberglass mesh assembly. In other embodiments, the mesh assembly is a wire mesh assembly. The fiberglass and the wire mesh assemblies are not meant to be limiting. In yet other embodiments, other suitable materials known to a person skilled in the art can be used to make the mesh assembly.

In step 130, the first mixture spread evenly over the mesh assembly is cured so that the encapsulating prepolymer is polymerized to form a sheet of composite core material comprising calcium sulfate discontinuous portions disposed in a continuous encapsulating resin. In certain embodiments, the sheet of composite core material has a thickness of about 0.0625 inches to about 1 inch. In some embodiments, the sheet of composite core material has a thickness of about 0.25 inches.

Figure 2:
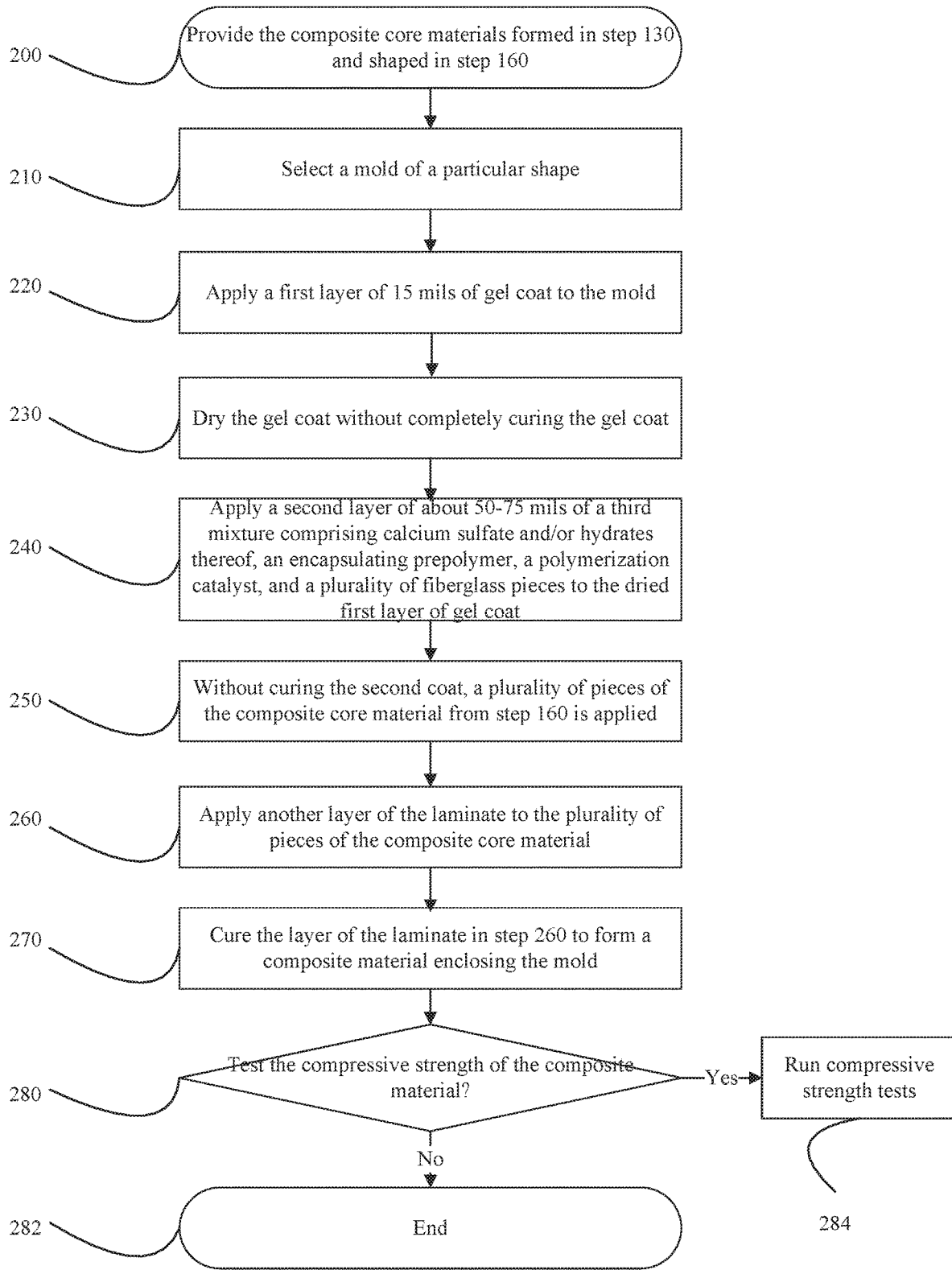
FIG. 2 is a flow chart of forming a composite product with a composite core material in FIG. 1.

Further, in step 140, a decision is made as to whether the sheet of the composite core material needs to be scored into a plurality of reinforcing blocks. In certain embodiments, smaller blocks of composite core materials are warranted. In step 150, the sheet of the composite core material is scored into a plurality of reinforcing blocks. In certain embodiments, each reinforcing block has a width of about 0.5 inches to about 4 inches and a length of about 0.5 inches to about 4 inches. In addition, in step 160, the sheet of the composite core material is cut into a plurality of pieces with any desirable length. In other embodiments, the sheet of composite core material is maintained in a solid sheet without scoring in step 152. For convenience of transportation, the sheet of composite core material can be cut into a smaller sheet of 48 inches wide by 48 inches long, 48 inches wide by 96 inches long, or any other width and length according to different requirements. FIG. 2 summarizes Applicant's method to utilize the composite core material that is described below in certain embodiments in manufacturing appliances, machines, automobiles, and etc. Referring to FIG. 2, in step 200, composite core materials formed in step 130 (FIG. 1) and shaped in step 130 or step 160 (FIG. 1) are provided.

In step 210, a mold of appliances, machines, automobiles, or etc. is provided. For example, if a user would like to build a bathtub incorporating the composite core materials, the user would start with a bathtub mold, i.e., a hollow form or matric for giving a particular shape of a bathtub. If a user would like to build a truck bed utilizing the composite core materials, the user would first supply a truck bed mold, i.e., a hollow form or matric for giving a particular shape of a truck bed.

After selecting a particular mold of a particular shape, a first layer of gel coat with a polymerization catalyst at a thickness of about 15 mils is applied to the mold in step 220. As described herein, "mil" is defined as a unit of length equal to about $\frac{1}{1000}$ inch used especially in measuring thickness (as of plastic films). The thickness of the gel coat is not limiting. According to the type of mold selected and strength requirement of the final product, the thickness of the gel coated applied varies accordingly. As a person skilled in the art would appreciate, a gel coat is a material used to provide a high-quality finish on a visible surface of a fiber-reinforced composite. The most common gel coats are based on epoxy or unsaturated polyester resin chemistry. Gel coats are modified resins which are applied to molds in the liquid state. They are cured to form crosslinked polymers and are subsequently backed with composite polymer matrices, often mixtures of polyester resin and fiberglass or epoxy resin with glass. The manufactured component, when sufficiently cured and removed from the mold, presents the gel coated surface. In certain embodiments, this is pigmented to provide a colored, glossy surface which improves the aesthetic appearance of the article, such as a counter made with cultured marble. In some embodiment, the first layer of gel coat is sprayed from a spraying apparatus onto the side of the selected mold from step 210. In other embodiments, the first layer of gel coat is brushed onto the selected mold from step 210. Other applying methods know to a person skilled in the art can be used herein. In certain embodiments, the polymerization catalyst has a concentration of about 1% to about 2.5% by weight in the mixture of the gel coat and the polymerization catalyst. The weight percentage of the polymerization catalyst can be about 1%, 1.25%, 1.5%, 1.75%, 2%, 2.25%, or any other weight percentage that ranges from 1% to 2.5%.

In step 230, the first layer of gel coat is dried but not completely cured on the side of the selected mold from step 210 at a temperature of about 100.degree. C. for about 5 minutes. The particular temperature and the length of time disclosed herein are not limiting, with various different types of gel coat applied, the particular temperature and the length of the time for curing vary accordingly.

After the first layer of gel coat is dried but not completely cured, in step 240, a second layer of laminate comprising of a third mixture is applied to the dried first layer of gel coat in step 230. Further, the third mixture comprises calcium sulfate and/or hydrates thereof, an encapsulating prepolymer, a polymerization catalyst, and a plurality of fiberglass pieces. In certain embodiments, the third mixture comprises about 50% to 54% of calcium sulfate and/or hydrates thereof, about 34% to 38% of the encapsulating prepolymer, and about 8% to 16% of the plurality of fiberglass pieces. In some embodiments, the third mixture comprises about 52.8% of calcium sulfate and/or hydrates thereof, about 35.2% of the encapsulating prepolymer, and about 12% of the plurality of fiberglass pieces. In certain embodiments, the polymerization catalyst has a concentration of about 1% to 2.5% by weight in the mixture of the encapsulating prepolymer and the polymerization catalyst. The weight percentage of the polymerization catalyst can be about 1%, 1.25%, 1.5%, 1.75%, 2%, 2.25%, or any other weight percentage that ranges from 1% to 2.5%.

Because the first layer of gel coat is not completely cured but dried, the first layer of gel coat is still sticky to the touch. When applying the second layer of laminate in step 240, the second layer of laminate does not leak through the dried first layer of gel coat. In certain embodiments, the second layer of laminate is applied at a thickness of about 50 to 75 mils. The thickness of the laminate layer is not limiting. According to the type of mold selected and strength requirement of the final product, the thickness of the laminate layer applied varies accordingly. Further, to ensure even application of the laminate layer, a suitable appliance is used to roll out any possible bubbles presented in the laminate layer.

In step 250, without solidifying the laminate layer in step 240, applying a plurality of pieces of the composite core materials from step 160 to the uncured laminate layer. Depends on different types of molds, sheets of the composite core materials from step 130 can applied to the uncured laminate layer. In certain embodiments, a thickness of about 50 mil of the composite core material is preferred. However, the thickness of the composite core material is not limiting. According to the type of mold selected and strength requirement of the final product, the thickness of the composite core material applied varies accordingly.

After applying pieces of the composite core material, another layer of the laminate is applied to pieces of composite core material in step 260. The laminate has the same composition as the laminate layer described in step 240. In certain embodiments, the thickness of the laminate layer in step 260 is about 50 to about 75 mil. Similarly, the thickness of the laminate layer is not limiting. According to the type of mold selected and strength requirement of the final product, the thickness of the laminate layer applied varies accordingly. After curing the second layer of laminate in step 260, a composite material incorporating the composite core materials is formed in step 270. The formed composite material encloses the mold selected in step 210.

Further, in step 280, a decision is made whether a compressive strength testing is needed on the piece of the composite material. If yes, step 280 transitions to step 284, one or more compressive strength tests will be carried out. If no, step 280 transitions to step 282. As described herein, compressive strength or compression strength is the capacity of a material or structure to withstand compressive loads, as opposed to tensile strength, which withstands loads tending to elongate. In other words, compressive strength resists compression (being pushed together), whereas tensile strength resists tension (being pulled apart). In the study of strength of materials, tensile strength, compressive strength, and shear strength can be analyzed independently.

Example 1

A compressive strength test is performed on the piece of the composite material formed in step 250. A 3 inch disc on a hydraulic cylinder applied compressive forces to the side of the piece of the composite material where the first and the second coats are both applied to test both deflection and bond strength of the piece of the composite material. The composite material did not fail when a pressure of 2,000 psi was applied.

While the preferred embodiments have been illustrated in detail, it should be apparent that modifications and adaptations to those embodiments may occur to one skilled in the art without departing from the scope of the claimed invention.

What is claimed is:

1. A method to form and utilize a composite core material, comprising:
    forming a sheet of a composite core material including curing the composite core material, wherein the composite core material is comprised of a mineral filler, an encapsulating resin, and a first polymerization catalyst, wherein the mineral filler comprises at least one of a calcium sulfate, a calcium carbonate, an aluminum trihydrate, a talc, a gypsum, a magnesium hydroxide, or a dolomite;
    forming a plurality of reinforcing blocks by scoring the sheet of the composite core material;
    applying a gel coat to a mold, wherein the gel coat includes a second polymerization catalyst;
    applying a layer of a laminate composition to the gel coat, wherein the laminate composition is comprised of a calcium sulfate, a second encapsulating resin, a third polymerization catalyst, and a plurality of fiberglass pieces;
    applying the plurality of reinforcing blocks to the layer of the laminate composition;
    applying another layer of the laminate composition to the plurality of reinforcing blocks; and
    curing the another layer of the laminate composition to form a composite material.

2. The method of claim 1, wherein the step of forming the sheet of the composite core material is comprised of mixing the mineral filler, the encapsulating resin, and the first polymerization catalyst.

3. The method of claim 2, wherein the first polymerization catalyst is comprised of 2-Butanone peroxide.

4. The method of claim 2, further comprising the step of polymerizing the encapsulating resin by curing the mineral filler, the encapsulating resin, and the first polymerization catalyst.

5. The method of claim 1, wherein the encapsulating resin and the second encapsulating resin are each selected from the group consisting of polyester resins, vinyl ester resins, fire retardant resins and any combinations thereof.

6. The method of claim 1, wherein the encapsulating resin and the second encapsulating resin are each comprised of a polyester resin.

7. The method of claim 1, wherein the mineral filler is selected from the group consisting of the calcium sulfate, the calcium carbonate, the aluminum trihydrate, the talc, the gypsum, the magnesium hydroxide, and the dolomite.

8. The method of claim 7, wherein the calcium sulfate comprises hydrates thereof, wherein the hydrates are selected from the group consisting of calcium sulfate hemihydrate having a formula of $CaSO_4 \cdot (nH_2O)$, wherein n is equal to or greater than 0.5 and equal to or less than 0.8; and calcium sulfate dihydrate having a formula of $CaSO_4 \cdot 2H_2O$.

9. The method of claim 1, wherein the sheet of composite core material has a thickness of 0.0625 inches to 1 inch.

10. The method of claim 1, wherein each of the plurality of reinforcing blocks has a width of 0.5 inches to 4 inches and a length of 0.5 inches to 4 inches.

11. A method of utilizing a composite core material, comprising the steps of:
    positioning a mesh assembly onto a moving belt;
    evenly spreading a mixture onto the mesh assembly when the mesh assembly is on the moving belt, wherein the mixture comprises a mineral filler, a polymerization catalyst, and an encapsulating resin, wherein the mineral filler comprises at least one of a calcium sulfate, a calcium carbonate, an aluminum trihydrate, a talc, a gypsum, a magnesium hydroxide, or a dolomite;
    curing the mixture on the mesh assembly to form a sheet of a composite core material comprising portions of the mineral filler disposed in the encapsulating resin;
    scoring the sheet of the composite core material into a plurality of reinforcing blocks;
    applying a gel coat to a mold, wherein the gel coat comprises a second polymerization catalyst;
    drying but not curing the gel coat on the mold;
    applying a first layer of a laminate composition to the gel coat after the gel coat has dried, wherein the laminate composition is comprised of calcium sulfate, the encapsulating resin, the polymerization catalyst, and a plurality of fiberglass pieces;
    applying the plurality of reinforcing blocks to the first layer of the laminate composition;
    applying a second layer of the laminate composition to the plurality of reinforcing blocks; and
    curing the second layer of the laminate composition to form a composite material enclosing the mold.

12. The method of claim 11, wherein the polymerization catalyst is comprised of 2-Butanone peroxide.

13. The method of claim 11, wherein the encapsulating resin is selected from the group consisting of polyester resins, vinyl ester resins, fire retardant resins and any combinations thereof.

14. The method of claim 11, wherein the mineral filler is selected from the group consisting of the calcium sulfate, the calcium carbonate, the aluminum trihydrate, the talc, the gypsum, the magnesium hydroxide, and the dolomite.

15. The method of claim 11, further comprising the step of heating the moving belt.

* * * * *